United States Patent [19]

Tolkoff et al.

[11] Patent Number: 5,256,158
[45] Date of Patent: Oct. 26, 1993

[54] DEVICE HAVING A RADIOPAQUE MARKER FOR ENDOSCOPIC ACCESSORIES AND METHOD OF MAKING SAME

[75] Inventors: M. Joshua Tolkoff, Brookline; Fernando Alvarez de Toledo, Concord, both of Mass.

[73] Assignee: ACT Medical, Inc., Watertown, Mass.

[21] Appl. No.: 702,621

[22] Filed: May 17, 1991

[51] Int. Cl.⁵ ............................................. A61H 25/00
[52] U.S. Cl. ...................................................... 604/280
[58] Field of Search ................. 604/96, 264, 280, 282; 128/656-658

[56] References Cited

U.S. PATENT DOCUMENTS

| | | |
|---|---|---|
| 4,195,637 | 3/1980 | Gruntzig . |
| 4,292,970 | 10/1981 | Hession, Jr. .................. 604/164 X |
| 4,323,071 | 3/1982 | Simpson et al. . |
| 4,516,970 | 5/1985 | Kaufman et al. ................ 604/270 |
| 4,545,390 | 10/1985 | Leary . |
| 4,661,094 | 4/1987 | Simpson ................................ 604/53 |
| 4,863,442 | 9/1989 | De Mello et al. ................. 604/282 |
| 4,920,980 | 5/1990 | Jackowski ......................... 128/786 |
| 4,967,753 | 11/1990 | Haase et al. ................... 128/662.06 |
| 5,045,071 | 9/1991 | McCormick et al. .............. 604/280 |

FOREIGN PATENT DOCUMENTS 0102685  5/1983  European Pat. Off. .
940777   7/1982  U.S.S.R. .............................. 128/658

OTHER PUBLICATIONS

Cook Urological Endoureterotomy Stent Sets data sheet, 1990.

Primary Examiner—C. Fred Rosenbaum
Assistant Examiner—C. Maglione
Attorney, Agent, or Firm—Lorusso & Loud

[57] ABSTRACT

A plastic catheter and a method for making the same, the catheter having radiopaque marker ring placed within a tube, whereby the radiopaque ring is inserted into the expanded section of the tube, followed by the relaxation of the tube to its original dimensions, such that there is no protusion of the ring on the tube innerdiameter, where the ring inner-diameter is equal or greater than the tube inner-diameter, and the ring outerdiameter protrudes a distance into the tube but not beyond the thickness of the tube; thereby, creating a smooth outer surface and an obstruction free inner surface.

6 Claims, 2 Drawing Sheets

DEVICE HAVING A RADIOPAQUE MARKER FOR ENDOSCOPIC ACCESSORIES AND METHOD OF MAKING SAME

BACKGROUND OF THE INVENTION

This invention relates generally to radiopaque markers for endoscopic accessories and method of making same, and more particularly concerns thin walled medical device tubes, such as endoscopic accessory catheters, having radiopaque marker rings placed inside the tube.

Tubes formed of Teflon polymer, and other thin walled medical device tubes are not radiopaque. To make them visible on x-rays for film or fluoroscopy, a number of different approaches are commonly used. A first method of making these tubes radiopaque is to add metal powder filler to the plastic medical device tube during processing. These metal powders include barium, bismuth, lead, tungsten, and tantalum. The limitations of this method are that the metal powder decreases the mechanical integrity of the tubing polymer. Thus, there is a limit to the amount of metal powder filler that can be added. The amount of metal powder filler is also limited because it is not the only filler used. In thin walled tubes, this greatly limits the "radio density" or visibility under x-ray that can be achieved. This renders most small thin walled tubes invisible under x-ray, even with metal powder fillers. An additional disadvantage to this method is that the metal powder fillers may be highly toxic. Therefore, they can cause harm if any of it should remain in the patient.

A second method of making a device radiopaque is to include metal markers on the outside of the thin walled tube. These markers can be pre-formed metal rings or wire wrapped rings. Here, the markers on the outside of the tube have adequate radiopacity, i.e., they provide good visibility under x-ray. However, attachment to the tube can be a limitation. Additionally, the marker is typically a metal ring that has a larger diameter than the plastic medical device tube. Therefore, the marker creates a small bump, or enlarged region which may catch on body tissues or the inside of other devices which the tube may be slid through.

Many techniques have been developed to overcome this problem. A first such technique is to stretch the plastic tube, place the metal ring over the stretched plastic tube, and then allowing the plastic tube to recover to its original size (this recovery occurs by relaxation, heat, etc.), thereby fixing the metal ring in place over the plastic tubing. A second technique is to bond the metal ring in place by use of adhesives, etc.. A third technique is to crimp the metal ring in place by using a swaging machine, crimping tool, or the like. A fourth technique is to cover the metal ring with a material which bonds to the plastic tube. This is particularly useful with balloon catheters. The sleeve or neck section of the balloon covers the ring. A fifth technique is to wrap a fine wire around the tube. Wire wrapping, however, has the same limitations as the pre-formed metal ring. Attachment is still difficult, and a bump or enlarged portion is still created at the location of the wire wrapping. In addition, the end of the wire is typically sharp and has to be finished to prevent harm to the patient. Also, the wire may have the tendency to "spring" back to its original, straight orientation, after winding onto the tube, causing it to enlarge or even come loose.

A third method of making a device radiopaque is to insert fine wire inside of an extra channel within the thin walled medical device tube. This method also has several disadvantages. Creating a separate channel in the plastic tubing makes it difficult to make small diameter tubing. Because the main channel, or lumen, of the tube is being used for the medical procedure, it must be as large as possible. Therefore, the separate channel must be made as small as possible. Because of the separate channel's small size, the radiopaque wire that passes through it is necessarily small as well. This limits the visibility of the wire under x-ray.

A fourth method is to add a radiopaque material into a matrix to add radiopacity. This can be done by placing powdered metal filler into an epoxy pre-polymer, and then applying the pre-polymer reactive mixture to the outside surface of the device, where it cures. This method also has several disadvantages. Firstly, the matrix decreases the mechanical integrity of the plastic tubing. Because of this, there is a limit to the size of the matrix that can be used, which, in turn, limits the visibility under x-ray that can be achieved. Additionally, the amount of metal powder filler that can be used is limited by the fact that other fillers will be used as well. This renders most small, thin wall tubes invisible under x-ray. Secondly, the use of a matrix increases the size of the tube because it creates a bump or enlarged region which may catch on body tissues or the inside of other devices.

All of these methods for making medical devices radiopaque have limitations when the device is Teflon polymer or Teflon polymer coated because Teflon polymer is not amenable to bonding.

Instead of the commonly used marker means, in the system of the present invention, a radiopaque marker ring is placed inside of the plastic medical tube. This has the advantage of creating a marker means that has good radiopacity and has a sound attachment of the marker means that becomes even more secure when the tube is stretched or bent. The dimensions of the radiopaque ring are such that other devices can slide through the tube without obstruction from the radiopaque ring. Placing the radiopaque ring inside of the tube in no way interferes with its function of locating the position of the ring during medical procedures, because it is just as radiopaque inside the tube as it is outside the tube.

Additionally, for an even more secure anchoring within the tube, the radiopaque ring can have one or both of its edges flared outward. This flared edge also allows for even easier passage of other devices through the ring. The radiopaque ring also serves other purposes. It can be used as an electrode within a medical device tube, which can be used, for example, as the catheter leads for heart stimulation and pacemakers. The radiopaque rings can also be used to provide support to the sides of the tube.

Additionally, it is possible to place more than one radiopaque ring within the medical device tube. It is also possible to insert the radiopaque rings in a tube that has more than one channel.

Accordingly, it is an object of the present invention to create a radiopaque marker with good radiopacity.

Yet another object of the invention is to provide a radiopaque marker in the form of a ring which will not cause a substantial protrusion on the outside of the tube in which it is located.

It is a further object of the present invention to create a radiopaque marker with good security of attachment.

It is still a further object of the present invention to create a radiopaque marker that is held even more securely when the tube is stretched or bent.

It is even still a further object of the present invention to create a radiopaque marker that does not cause a partial obstruction inside of the tube, and cannot be pushed out of the tube by a wire or other device moving through the tube.

It is even still a further object of the present invention to create a radiopaque marker with the above identified advantages, that can be easily constructed.

SUMMARY OF THE INVENTION

The foregoing objects are achieved in accordance with the present invention by placing a radiopaque ring inside the catheter tubing.

BRIEF DESCRIPTION OF THE DRAWINGS

Other objects and advantages of the invention will become apparent upon reading the following detailed description and upon reference to the drawings, in which.

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

DESCRIPTION OF THE PREFERRED EMBODIMENT

Figure 1:
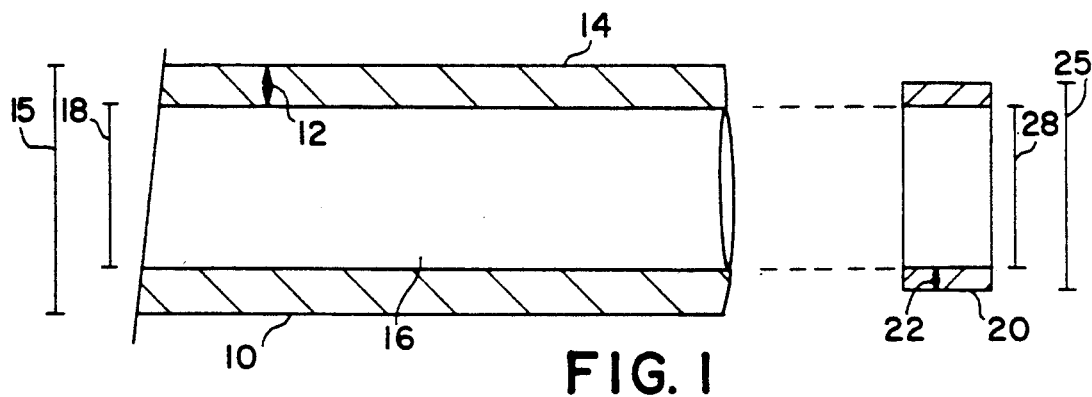
FIG. 1 is a cut-away side view of a plastic tube and a radiopaque marker prior to the markers insertion in the tube.

Turning first to FIG. 1, there is shown a tube (10) that is typically used in medical procedures involving endoscopic tubes. Such a tube (10) is generally made of flexible plastic, TFE (Teflon) or TFE coated plastic. The tube (10) is manufactured with specific dimensions, which include tube wall-thickness (12), tube outer-diameter (15), and tube inner-diameter (18).

Figure 5:
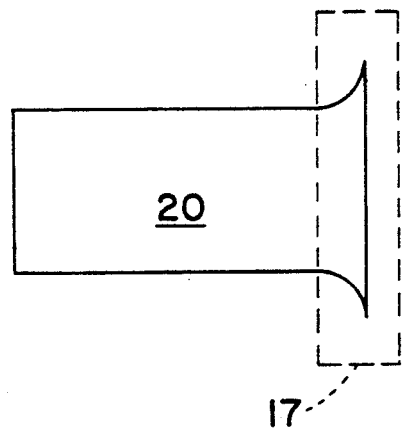
FIG. 5 is a side view of a radiopaque marker ring with one of its edges flared outward.

Also shown in FIG. 1 is radiopaque ring (20), which is a circular ring. The radiopaque ring (20) can be made of a radiopaque material such as bismuth, lead, tungsten, etc., but is preferably made a non-toxic radiopaque material such as tantalum. As with the tube (10), the radiopaque ring (20) is also manufactured with specific dimensions. These dimensions include ring wall-thickness (22), ring outer-diameter (25), and ring inner-diameter (28). The dimensions for the radiopaque ring (20) and tube (10) are carefully selected such that ring inner-diameter (28) is equal to or larger than the tube inner-diameter (18). In a preferred embodiment, the radiopaque ring (20), as shown in FIG. 5, can have a flared edge (17). This flared edge (17) allows for better anchoring in the tube (10). It also allows for other devices to slide through the tube (10) without interference.

Figure 2:
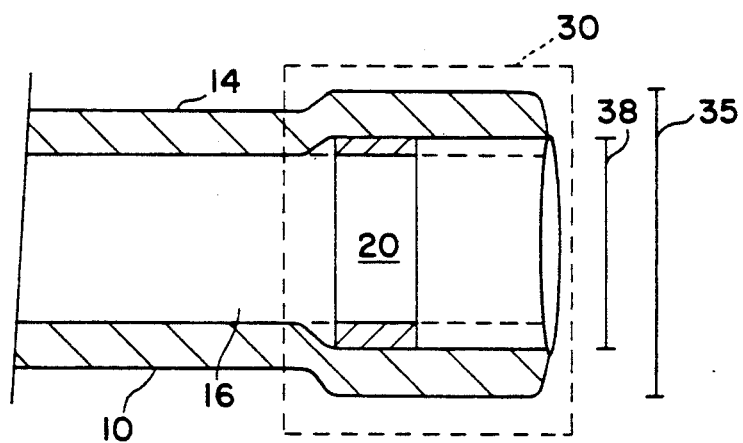
FIG. 2 is a cut-away side view of an intermediate manufacturing step in which a radiopaque marker has been inserted into the tube.

The first step in the manufacturing process is to insert the radiopaque ring (20) into the lumen (16) of the tube (10). As shown in FIG. 2, this is accomplished by creating an expanded-end-section (30) on the tube (10). The expanded-end-section (30) is characterized by having an expanded inner-diameter (38) that is equal to or greater than the ring outer diameter (25). An expanded outer-diameter (35) is also created. The expanded-end-section (30) can be created by numerous methods. One such method is to heat the tube (10), until soft, but not melt, which will cause the plastic, or other material used to expand. Another method is to mechanically expand the tube (10) with various tools. When the tube (10) has expanded such that it has reached the proper dimensions for the expanded-end-section (30), the radiopaque ring (20) can be easily inserted into the expanded-end-section (30) of the tube (10).

Figure 3:
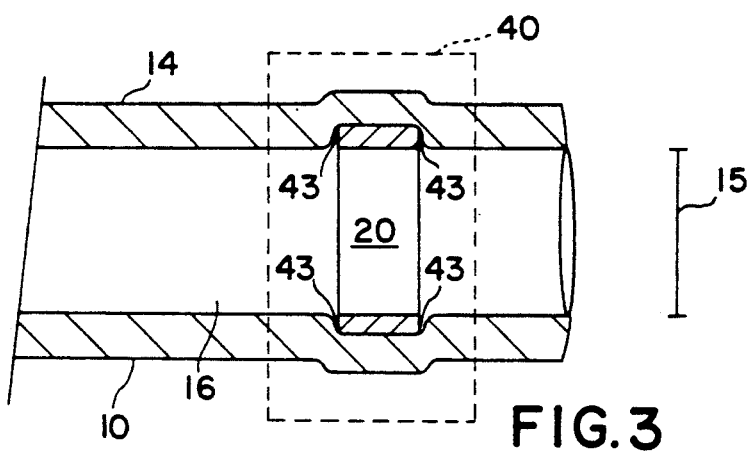
FIG. 3 is a cut-away side view of the tube after the radiopaque marker has been inserted within the tube.

After the radiopaque ring (20) has been inserted in the expanded-end-section (30) of the tube (10), it is desired to have the tube (10) return to its original dimensions, i.e., shrink or relax. The manner in which this occurs depends on how the expanded-end-section (30) was created. If the expanded-end-section (30) was created by heating the tube (10), the cooling of the tube (10) will allow the expanded-end-section (30) to shrink, and return to its original dimensions. If the expanded-end-section (30) was created mechanically, the natural elasticity of the tube's (10) material will force it to relax, and return to its original dimensions. As shown in FIG. 3, because the tube (10) has returned to its original dimensions, the tube inner-diameter (18) is the same on each side of the radiopaque ring (20). Therefore, the tube inner-diameter (18) is also equal to or less than the ring inner-diameter (28). This is highly advantageous because it allows various endoscopic medical devices to pass through the tube (10) unobstructed by any radiopaque rings (20). An additional advantage of this method is that the tube (10), upon relaxation, acts to surround the radiopaque ring (20), forming a tube-ring-sleeve (43). This tube-ring-sleeve (43) acts as a trap to hold the radiopaque ring (20) in place, and has the great advantage of preventing the radiopaque ring (20) from being pushed out of the tube (10) by a wire, or any other device moving through the tube (10). Additionally, due to the tube's (10) elasticity, and because the radiopaque ring (20) is embedded within the tube-ring-sleeve (43), stretching or bending the tube (10) will result in an even tighter grip of the radiopaque ring (20).

Figure 4:
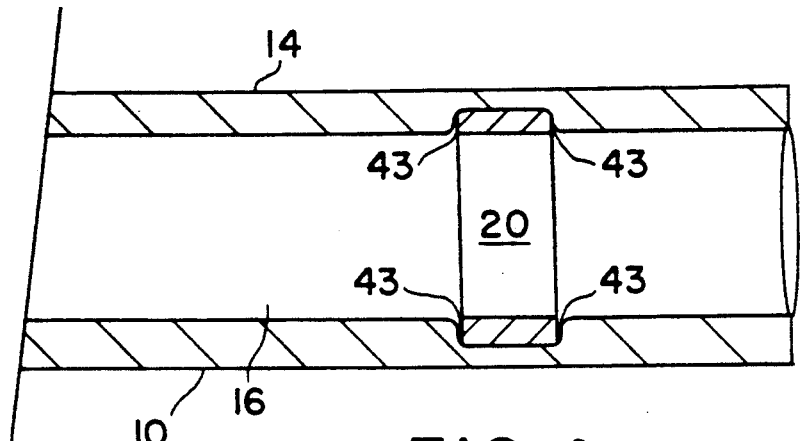
FIG. 4 is a cut-away side view of a completed tube.

As also shown in FIG. 3, however, it is seen that while the expanded-end-section (30) has been eliminated, a small bump (40) still exists on the outer-surface (14) of the tube (10) where the radiopaque ring (20) has been inserted. This is due to the ring wall-thickness (22) being added to the tube wall-thickness (12). This is not desirable. As smooth an outer-surface (14) as possible is required in order to avoid injury and discomfort to the patient and to smoothly fit through other devices. It is therefore desirable to eliminate the bump (40). It is possible to substantially eliminate the bump (40) by the use of a swager, crimper or heated die. After substantial elimination of the bump (40), the outer-surface (14) of the tube (10) will be substantially smooth, as shown in FIG. 4.

Typical dimensions for the tube outer-diameter (15) are 0.065 inches to 0.105 inches. Typical dimensions for the tube inner-diameter (18) and ring inner-diameter (28) are 0.040 inches to 0.060 inches. Typical dimensions for the tube wall-thickness (12) are 0.010 inches to 0.30 inches. Typical dimensions for the ring wall-thickness (22) are 0.003 inches to 0.006 inches. The length of the radiopaque ring (20) is typically 0.60 inches to 0.080 inches. Of course, these are only typical ranges. The actual dimensions used can be both larger and smaller than those given.

Thus it is apparent that there has been provided, in accordance with the invention, a radiopaque marker for endoscopic accessories and a method for making them that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A device having a radiopaque marker ring for use with endoscopic accessories comprising:
a tube defining a lumen and a radiopaque ring, wherein said tube has a tube inner-diameter and a tube outer-diameter and said radiopaque ring has a ring inner-diameter and a ring outer-diameter, such that said ring inner-diameter is equal to said tube inner-diameter, but that said ring outer-diameter is less than said tube outer-diameter, wherein said ring is disposed completely within said lumen of the tube, a distance away from either end of said tube, and detached from objects other than the tube, wherein said ring, having an inner and outer surface, is positioned such that said inner surface of said ring is exposed to said lumen of said tube and said outer surface of said ring is embedded within said tube, so that said tube with said radiopaque ring presents a continuous, non-obstructed, pathway and a smooth, bump-free inner and outer surface, and the overall thickness of said tube, caused by the inclusion therein of said marker ring, is minimized.

2. The device of claim 1, wherein said tube is a catheter constructed of a flexible plastic material.

3. The device of claim 1, wherein said tube is a catheter constructed of flexible TFE material.

4. The device of claim 1, wherein said tube is a catheter constructed of a flexible plastic material and coated with TFE.

5. The device of claim 1, wherein said tube with said radiopaque ring disposed within said tube has a smooth outer surface.

6. A method of constructing a device having a radiopaque marker for use in endoscopic accessories comprising:
providing a tube;
expanding said tube to create an expanded-end-section;
inserting a radiopaque ring, having an inner and outer surface, inside said expanded-end-section of said tube, such that said ring inner-surface is exposed to the said lumen of said tube and said ring outer-surface is embedded in said tube;
shrinking said expanded-end-section so that said tube returns to its original dimensions.

* * * * *